(12) United States Patent
Litvak

(10) Patent No.: US 9,403,005 B2
(45) Date of Patent: *Aug. 2, 2016

(54) SYSTEMS AND METHODS FOR OPTIMIZING A COMPLIANCE VOLTAGE OF AN AUDITORY PROSTHESIS

(71) Applicant: Advanced Bionics AG, Staefa (CH)

(72) Inventor: Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/755,869

(22) Filed: Jun. 30, 2015

(65) Prior Publication Data

US 2015/0297891 A1    Oct. 22, 2015

Related U.S. Application Data

(63) Continuation-in-part of application No. 14/712,828, filed on May 14, 2015, which is a continuation of application No. 14/114,907, filed as application No. PCT/US2011/034860 on May 2, 2011, now Pat. No. 9,036,846.

(51) Int. Cl.
*H04R 25/00* (2006.01)
*A61N 1/36* (2006.01)
(Continued)

(52) U.S. Cl.
CPC .............. *A61N 1/36032* (2013.01); *A61N 1/36* (2013.01); *H04R 25/554* (2013.01); *H04R 25/606* (2013.01); *A61N 1/025* (2013.01); *A61N 1/0541* (2013.01); *H04R 2225/67* (2013.01)

(58) Field of Classification Search
CPC .... H04R 25/353; H04R 25/505; H04R 25/55; H04R 25/554; H04R 25/606; H04R 2225/67; A61N 1/36032; A61N 1/36

USPC ........ 381/23.1, 312, 316, 317, 320, 321, 326, 381/328, 94.2, 94.3, 94.7; 600/25; 607/55, 607/56, 57

See application file for complete search history.

(56) References Cited

U.S. PATENT DOCUMENTS 7,242,985 B1  7/2007  Fridman et al.
7,251,530 B1  7/2007  Overstreet et al.
(Continued)

FOREIGN PATENT DOCUMENTS

WO    WO-2010/028152    3/2010

OTHER PUBLICATIONS

International Search Report and Written Opinion received in International Application No. PCT/US2011/034860 dated Sep. 6, 2011.
(Continued)

*Primary Examiner* — Huyen D Le
(74) *Attorney, Agent, or Firm* — ALG Intellectual Property, LLC

(57) ABSTRACT

An exemplary sound processor 1) sets a current steering range for a stimulation channel defined by first and second physical electrodes communicatively coupled to an auditory prosthesis to be less than an entire physical range of the stimulation channel, 2) maps each frequency included in a frequency band associated with the stimulation channel to a virtual electrode included in a plurality of virtual electrodes included in the current steering range of the stimulation channel, 3) identifies a feature of an audio signal, 4) identifies a virtual electrode included in the plurality of virtual electrodes and that is associated with the identified feature, and 5) directs the auditory prosthesis to apply electrical stimulation representative of the identified feature to a stimulation site associated with the identified virtual electrode by concurrently stimulating the first physical electrode with a first current level and the second physical electrode with a second current level.

20 Claims, 8 Drawing Sheets

(51) Int. Cl.
*A61N 1/02* (2006.01)
*A61N 1/05* (2006.01)

(56) References Cited

U.S. PATENT DOCUMENTS

| | | | |
|---|---|---|---|
| 7,277,760 B1 | 10/2007 | Litvak et al. | |
| 7,317,945 B2* | 1/2008 | Litvak | A61N 1/36032 607/57 |
| 8,422,706 B2* | 4/2013 | Kulkarni | A61N 1/36032 381/317 |
| 9,036,846 B2* | 5/2015 | Litvak | A61N 1/36032 381/312 |
| 2004/0136556 A1 | 7/2004 | Litvak et al. | |
| 2005/0137651 A1 | 6/2005 | Litvak et al. | |
| 2006/0100672 A1 | 5/2006 | Litvak | |
| 2009/0222064 A1 | 9/2009 | Faltys et al. | |
| 2010/0161000 A1 | 6/2010 | Litvak et al. | |
| 2010/0228321 A1 | 9/2010 | Litvak et al. | |
| 2011/0064241 A1 | 3/2011 | Kulkarni | |
| 2011/0077710 A1 | 3/2011 | Saoji et al. | |
| 2011/0098785 A1 | 4/2011 | Mishra | |

OTHER PUBLICATIONS

Zierhofer, et al., "Simultaneous Intracochlear Stimulation Based on Channel Interaction Compensation: Analysis and First Results", *IEEE Transations on Biomedical Engineering*, vol. 55, No. 7, Jul. 2008.

Communication pursuant to Article 94(3) EPC received in European Patent Application No. 11721161.5, dated Dec. 23, 2014.

Communication pursuant to Article 94(3) EPC received in European Patent Application No. 11721161.5 dated Nov. 6, 2015.

Non-Final Office Action received in U.S. Appl. No. 14/712,828 dated Feb. 26, 2016.

\* cited by examiner

SYSTEMS AND METHODS FOR OPTIMIZING A COMPLIANCE VOLTAGE OF AN AUDITORY PROSTHESIS

RELATED APPLICATIONS

The present application is a continuation-in-part application of U.S. application Ser. No. 14/712,828, filed May 14, 2015, which application is a continuation application of U.S. patent application Ser. No. 14/114,907, filed Oct. 30, 2013, which application issued as U.S. Pat. No. 9,036,846 on May 19, 2015 and is a U.S. National Stage Entry of PCT Application No. PCT/US11/34860, filed May 2, 2011. The contents of these applications are incorporated herein by reference in their respective entireties.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be helped by the use of conventional hearing aids that amplify sound so that audio signals reach the cochlea and the hair cells. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to stimulation sites (e.g., auditory nerve fibers) by way of one or more channels formed by an array of electrodes implanted in an auditory prosthesis patient. Direct stimulation of the stimulation sites leads to the perception of sound in the brain and at least partial restoration of hearing function.

Some conventional auditory prosthesis systems may be configured to use current steering to apply electrical stimulation to stimulation sites not directly associated with the electrodes implanted within an auditory prosthesis patient. For example, an auditory prosthesis system may concurrently stimulate multiple (e.g., two) electrodes that surround, but that are not directly associated with, a particular stimulation site in order to steer current to (and thereby apply electrical stimulation to) the stimulation site. One advantage of current steering is that the current used to concurrently stimulate the multiple electrodes is split between the multiple electrodes, thereby reducing the compliance voltage (i.e., the voltage maintained by the auditory prosthesis that governs a maximum level of stimulation current that can be delivered by the auditory prosthesis) required to generate the current. Unfortunately, however, even when current steering is used in a conventional auditory prosthesis system, the auditory prosthesis has to maintain a relatively high compliance voltage to account for situations in which the desired stimulation site is directly associated with a single electrode. In such situations, a relatively high compliance voltage is required because all of the current is applied to the single electrode.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for optimizing a compliance voltage of an auditory prosthesis (e.g., an implantable cochlear stimulator) are described herein. As will be described below, each stimulation channel formed by electrodes that are coupled to an auditory prosthesis may have an adjustable current steering range associated therewith. Each adjustable current steering range is centered about the midpoint of its respective stimulation channel and defines a range of current steering that may be used within its respective stimulation channel. A compliance voltage of an auditory prosthesis may be optimized by setting a current steering range for one or more stimulation channels to a value that results in an optimum balance between power conservation and performance of the auditory prosthesis.

To illustrate, the current steering range associated with one or more stimulation channels may be decreased in order to decrease the compliance voltage required by an auditory prosthesis and thereby decrease the amount of power consumed by the auditory prosthesis. However, because the range of current steering that may be used by the auditory prosthesis is also reduced as the current steering range is decreased, an overall performance level of the auditory prosthesis may also be decreased as the current steering range is decreased. Hence, in some examples (e.g., when power conservation is relatively less important than performance), the compliance voltage may be optimized by increasing the current steering range associated with one or more stimulation channels in order to increase a performance level of the auditory prosthesis.

Figure 1:
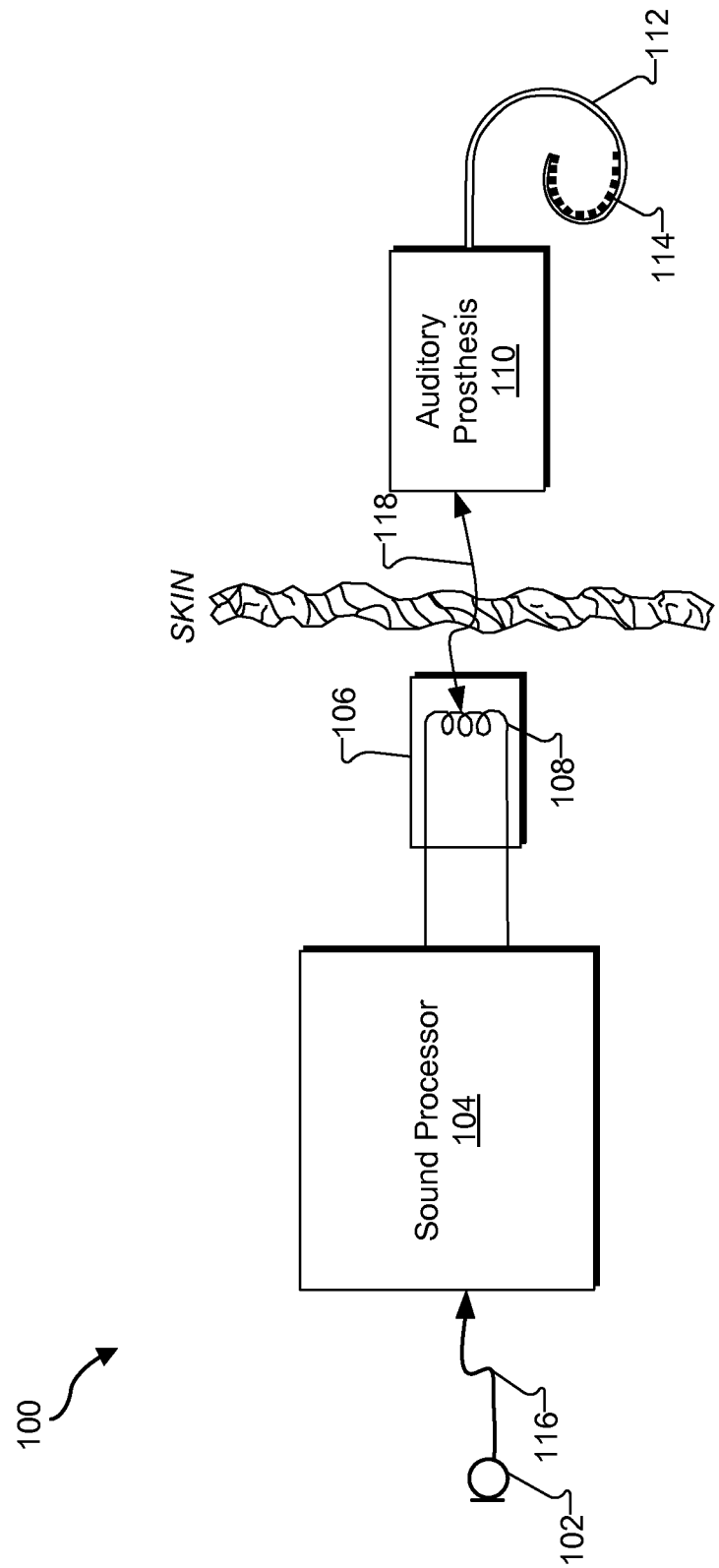
FIG. 1 illustrates an exemplary auditory prosthesis system according to principles described herein.

FIG. 1 illustrates an exemplary auditory prosthesis system 100. Auditory prosthesis system 100 may include a microphone 102, a sound processor 104, a headpiece 106 having a coil 108 disposed therein, an auditory prosthesis 110, and a lead 112 with a plurality of electrodes 114 disposed thereon. Additional or alternative components may be included within auditory prosthesis system 100 as may serve a particular implementation.

As shown in FIG. 1, microphone 102, sound processor 104, and headpiece 106 may be located external to an auditory prosthesis patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct auditory prosthesis 110 to generate and apply electrical stimulation (also referred to herein as "stimulation current") to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the audio signal detected by microphone 102 in accordance with a selected sound processing strategy to generate appropriate stimulation parameters for controlling auditory prosthesis 110. Sound processor 104 may include or be implemented by a behind-the-ear ("BTE") unit, a body-worn portable speech processor ("PSP"), and/or any other sound processing unit as may serve a particular implementation. Exemplary components of sound processor 104 will be described in more detail below.

Sound processor 104 may be configured to transcutaneously transmit one or more control parameters and/or one or more power signals to auditory prosthesis 110 with coil 108 by way of a communication link 118. These control parameters may be configured to specify one or more stimulation parameters, operating parameters, and/or any other parameter by which auditory prosthesis 110 is to operate as may serve a particular implementation. Exemplary control parameters include, but are not limited to, stimulation current levels, volume control parameters, program selection parameters, operational state parameters (e.g., parameters that turn a sound processor and/or an auditory prosthesis on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters. Additional features of sound processor 104 will be described in more detail below.

As shown in FIG. 1, coil 108 may be housed within headpiece 106, which may be affixed to a patient's head and positioned such that coil 108 is communicatively coupled to a corresponding coil included within auditory prosthesis 110. In this manner, control parameters and power signals may be wirelessly transmitted between sound processor 104 and auditory prosthesis 110 via communication link 118. It will be understood that data communication link 118 may include a bi-directional communication link and/or one or more dedicated uni-directional communication links. In some alternative embodiments, sound processor 104 and auditory prosthesis 110 may be directly connected with one or more wires or the like.

Auditory prosthesis 110 may include any type of implantable stimulator that may be used in association with the systems and methods described herein. For example, auditory prosthesis 110 may include an implantable cochlear stimulator. In some alternative implementations, auditory prosthesis 110 may include a brainstem implant and/or any other type of auditory prosthesis that may be implanted within a patient and configured to apply stimulation to one or more stimulation sites located along an auditory pathway of a patient.

In some examples, auditory prosthesis 110 may be configured to generate electrical stimulation representative of an audio signal detected by microphone 102 in accordance with one or more stimulation parameters transmitted thereto by sound processor 104. Auditory prosthesis 110 may be further configured to apply the electrical stimulation to one or more stimulation sites within the patient via one or more stimulation channels formed by electrodes 114 disposed along lead 112.

Figure 2:
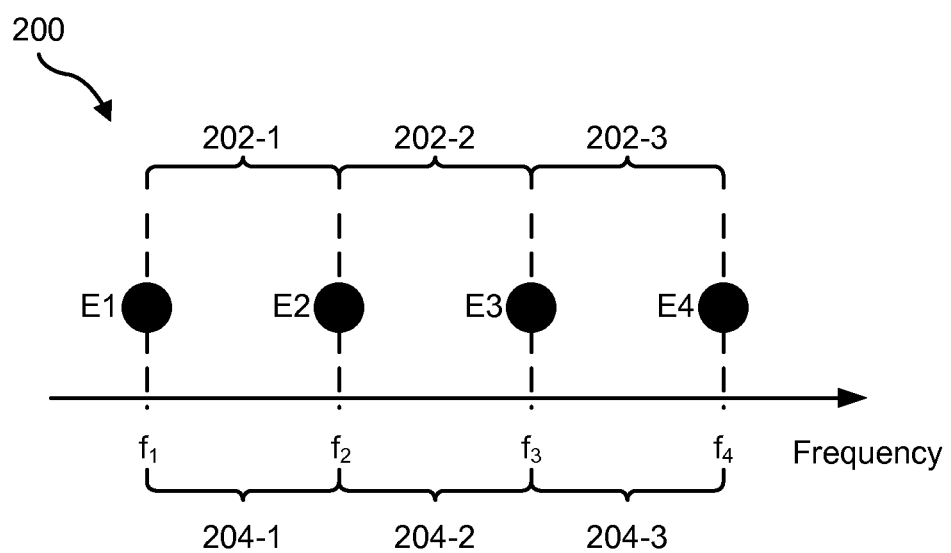
FIG. 2 shows a plurality of electrodes that define a plurality of stimulation channels according to principles described herein.

To illustrate, FIG. 2 shows a plurality of electrodes E1-E4 (also referred to herein as "physical electrodes") that define a plurality of stimulation channels 202-1 through 202-3 (collectively "stimulation channels 202"). Physical electrodes E1 and E2 define a first stimulation channel 202-1, physical electrodes E2 and E3 define a second stimulation channel 202-2, and physical electrodes E3 and E4 define a third stimulation channel 202-3. Each stimulation channel 202 may have a particular frequency band 204 (e.g., frequency bands 204-1 through 204-3) associated therewith. For example, frequency band 204-1 comprises frequencies $f_1$ through $f_2$ and is associated with stimulation channel 202-1, frequency band 204-2 comprises frequencies $f_2$ through $f_3$ and is associated with stimulation channel 202-2, and frequency band 204-3 comprises frequencies $f_3$ through $f_4$ and is associated with stimulation channel 202-3. As will be described below, a frequency associated with (e.g., included within) an audio signal and included within a particular frequency band (e.g., frequency band 204-1) may be represented by stimulating one or more of the physical electrodes (e.g., physical electrodes E1 and/or E2) that define the stimulation channel (e.g., stimulation channel 202-1) associated with the particular frequency band.

Figure 3:
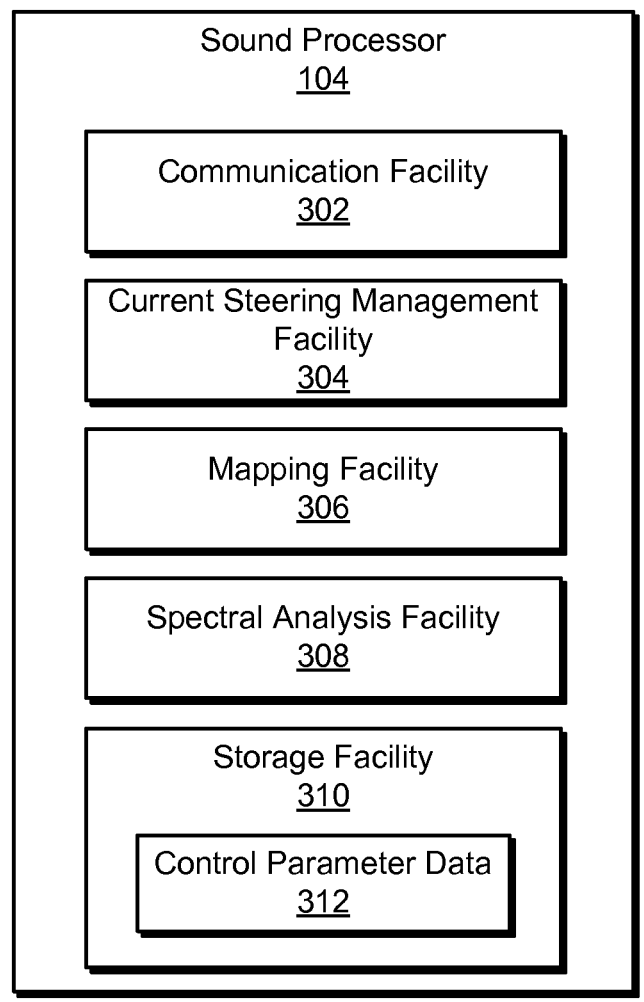
FIG. 3 illustrates exemplary components of a sound processor according to principles described herein.

FIG. 3 illustrates exemplary components of sound processor 104. As shown in FIG. 3, sound processor 104 may include a communication facility 302, a current steering management facility 304, a mapping facility 306, a spectral analysis facility 308, and a storage facility 310, which may be in communication with one another using any suitable communication technologies. Each of these facilities 302-310 may include any combination of hardware, software, and/or firmware as may serve a particular implementation. For example, one or more of facilities 302-310 may include a computing device or processor configured to perform one or more of the functions described herein. Facilities 302-310 will now be described in more detail.

Communication facility 302 may be configured to facilitate communication between sound processor 104 and auditory prosthesis 110. For example, communication facility 302 may include transceiver components configured to wirelessly transmit data (e.g., control parameters and/or power signals) to auditory prosthesis 110 and/or wirelessly receive data from auditory prosthesis 110.

Current steering management facility 304 may be configured to perform one or more current steering management operations. For example, current steering management facility 304 may be configured to determine, set, adjust, or otherwise modify a current steering range for a stimulation channel defined by first and second physical electrodes communicatively coupled to an auditory prosthesis.

Figure 4:
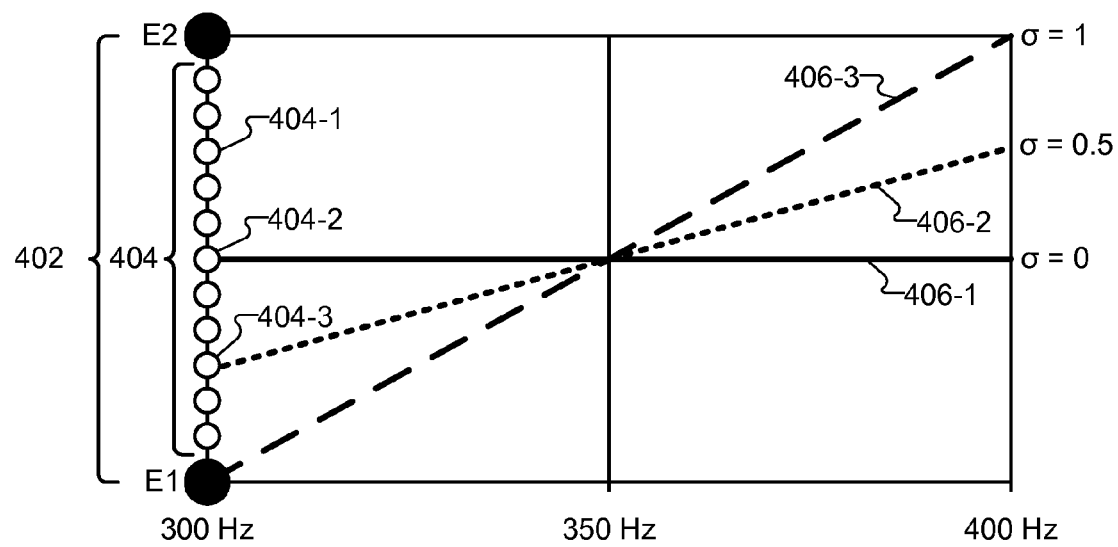
FIG. 4 shows a particular stimulation channel defined by first and second physical electrodes according to principles described herein.

As mentioned, a current steering range associated with a stimulation channel may be centered about the midpoint (which may be the arithmetic mean or the geometric mean) of the stimulation channel and defines a range of current steering that may be used within the stimulation channel. To illustrate, FIG. 4 shows a particular stimulation channel 402 defined by first and second physical electrodes E1 and E2. Stimulation channel 402 may be associated with any frequency band as may serve a particular implementation. In the example of FIG. 4, stimulation channel 402 is associated with a frequency band having a minimum frequency of 300 Hz and a maximum frequency of 400 Hz. It will be recognized that the current steering range may alternatively be centered about any other point within the stimulation channel as may serve a particular implementation.

As shown, stimulation channel 402 may be conceptualized as having a plurality of virtual electrodes 404 (e.g., virtual electrodes 404-1, 404-2, and 402-3) disposed in between physical electrodes E1 and E2. Each virtual electrode 404 represents a particular location along an electrode lead (e.g., lead 112) and in between physical electrodes E1 and E2. For example, virtual electrode 404-2 represents a midpoint of stimulation channel 402 about which a current steering range associated with stimulation channel 402 is centered.

The current steering range associated with stimulation channel 402 may include any number of the virtual electrodes 404 included in stimulation channel 402, and, in some instances, may also include physical electrodes E1 and E2. In some examples, the current steering range associated with stimulation channel 402 may be set by setting a corresponding current steering range value to any value in between and including zero and one. For example, a current steering range value may be set to zero to minimize the current steering range about the midpoint of stimulation channel 402 (i.e., only include virtual electrode 404-2) and thereby direct the auditory prosthesis to not use current steering about the midpoint of stimulation channel 402. In other words, any frequency included in the frequency band associated with stimulation channel 402 (i.e., any frequency in between and including 300 Hz and 400 Hz) is represented by concurrently stimulating the first and second physical electrodes E1 and E2 with a substantially equal amount of current.

Alternatively, the current steering range value associated with stimulation channel 402 may be set to one to maximize the current steering range about the midpoint of stimulation channel 402 (i.e., set the current steering range to be substantially equal to an entire physical range of stimulation channel 402, which includes both physical electrodes E1 and E2 as well as all of the virtual electrodes 404 disposed therebetween) and thereby direct the auditory prosthesis to use full current steering about the midpoint of stimulation channel 402. In other words, each frequency in between (but not including) a minimum frequency (i.e., 300 Hz) and a maximum frequency (i.e., 400 Hz) included in a frequency band associated with the stimulation channel is represented by concurrently stimulating the first and second physical electrodes E1 and E2 with a unique ratio of current. However, the minimum frequency (i.e., 300 Hz) is represented by applying all of the current to the first physical electrode E1 and the maximum frequency (i.e., 400 Hz) is represented by applying all of the current to the second physical electrode E2.

The current steering range value associated with stimulation channel 402 may be set to any other value in between zero and one in order to set the current steering range to any other range within the physical range of stimulation channel 404.

In some examples, current steering management facility 304 may set a current steering range for a particular stimulation channel to be less than an entire physical range of the stimulation channel. In this manner, as will be described below, current steering management facility 304 may ensure that current is always split between the two physical electrodes that define the stimulation channel, thereby reducing the compliance voltage needed to generate the current. As will be described below, a reduced compliance voltage may result in the auditory prosthesis consuming a reduced amount of power.

In some examples, current steering management facility 304 may set a single current steering range and apply the single current steering range to a plurality of stimulation channels (e.g., all of the stimulation channels associated with auditory prosthesis 110). Alternatively, current steering management facility 304 may set a unique current steering range for each stimulation channel associated with auditory prosthesis 110.

In some examples, current steering range management facility 304 may set a current steering range in response to input provided to sound processor 104 by a user. Additionally or alternatively, as will be described below, current steering range management facility 304 may automatically set a current steering range in response to one or more factors. For example, as will be described in more detail below, current steering range management facility 304 may determine a relative importance of performance versus power conservation for auditory prosthesis 110 and set the current steering range in accordance with the determined relative importance. As another example, current steering range management facility 304 may detect a change (e.g., a decrease) in power available to auditory prosthesis 110 and adjust (e.g., decrease) the current steering range in response to the change in available power. Additional current steering management operations that may be performed by current steering management facility 304 will be described below.

Returning to FIG. 3, mapping facility 306 may be configured to map the frequencies included a frequency band associated with a stimulation channel to one or more electrodes (physical and/or virtual) included in the current steering range of the stimulation channel. To illustrate, with reference again to FIG. 4, each frequency in between and including 300 Hz and 400 Hz may be mapped to physical electrodes E1 and E2 and/or any number of virtual electrodes 404 in accordance with a current steering range set by current steering range management facility 304 for stimulation channel 402.

For example, line 406-1 represents an exemplary frequency-to-electrode mapping when the current steering range value (referred to as "σ" in FIG. 4) has been set to zero. In this case, the current steering range is limited to include only the virtual electrode (i.e., virtual electrode 404-2) located at the midpoint of stimulation channel 404. Hence, as illustrated by line 406-1, each frequency in between and including 300 Hz and 400 Hz is mapped to virtual electrode 404-2.

Two additional frequency-to-electrode mappings are also illustrated in FIG. 4. For example, line 406-2 represents an exemplary frequency-to-electrode mapping when the current steering range value has been set to 0.5. In this case, the current steering range is limited to half of the entire physical range of stimulation channel 402 and includes virtual electrodes 404-1 and 404-3 as well as the virtual electrodes 404 disposed therebetween. Hence, as illustrated by line 406-2, each frequency in between and including 300 Hz and 400 Hz is mapped to any of these virtual electrodes 404.

Likewise, line 406-3 represents an exemplary frequency-to-electrode mapping when the current steering range value has been set to one. In this case, the current steering range is substantially equal to an entire physical range of stimulation channel 402 and includes physical electrodes E1 and E2 as well as the virtual electrodes 404 disposed therebetween. Hence, as illustrated by line 406-3, 300 Hz is mapped to physical electrode E1, 400 Hz is mapped to physical electrode E2, and each frequency in between 300 Hz and 400 Hz is mapped to virtual electrodes 404.

Returning to FIG. 3, spectral analysis facility 308 may be configured to identify a feature of an audio signal presented to an auditory prosthesis patient. As will be described below, this feature may be used to identify a virtual electrode that is to be stimulated by auditory prosthesis 110.

Spectral analysis facility 308 may identify any suitable feature of an audio signal as may serve a particular implementation. For example, spectral analysis facility 308 may identify one or more frequencies (e.g., a dominant frequency) associated with (e.g., included within) an audio signal presented to an auditory prosthesis patient.

Spectral analysis facility 308 may detect one or more frequencies associated with an audio signal in any suitable manner as may serve a particular implementation. For example, spectral analysis facility 308 may be implemented by a plurality of band-pass filters configured to divide the audio signal into a plurality of frequency bands. Additionally or alternatively, spectral analysis facility 308 may be configured to convert the audio signal from a time domain into a frequency domain and then divide the resulting frequency bins into the plurality of frequency bands. To this end, spectral analysis facility 308 may include one or more components configured to apply a Discrete Fourier Transform (e.g., a Fast Fourier Transform ("FFT")) to the audio signal.

In some examples, spectral analysis facility 308 may be configured to analyze an acoustic spectrum of an audio signal and identify a spectral peak included therein. Spectral analysis facility 308 may then designate a frequency of the spectral peak as the dominant frequency.

As another example, spectral analysis facility 308 may identify a feature of an audio signal by identifying a pitch of the audio signal. As used herein, "pitch" refers to a percept of what a person may actually hear when the audio signal is presented to the person. In some examples, an audio signal may have different frequency components that together create a perception of a particular frequency by the person.

Hence, spectral analysis facility 308 may identify a pitch of an audio signal by identifying a plurality of spectral peaks included in the audio signal, identifying a plurality of frequencies corresponding to the plurality of spectral peaks, and identifying the pitch based on the plurality of frequencies. This analysis may include an analysis of harmonics and their spacing, and/or any other signal processing technique configured to identify pitch as may serve a particular implementation. Once the pitch is identified, current steering management facility 304 may identify a virtual electrode that corresponds to the pitch by identifying one or more virtual electrodes that correspond to one or more of the frequencies that correspond to the identified spectral peaks.

In some examples, spectral peaks may be included in an audio signal that are not associated with the pitch of the audio signal. To avoid including these spectral peaks in those that are used to identify the pitch of the audio signal, spectral analysis facility 308 analyze one or more pitches of the audio signal during one or more stimulation frames that temporally precede the current stimulation frame. This may provide some temporal context to what the pitch probably should be during the current stimulation frame.

As another example, spectral analysis facility 308 may identify a feature of an audio signal by determining an average frequency of the audio signal within the frequency band associated with the stimulation channel. The average frequency may be determined in any suitable manner. For example, the average frequency may be determined by identifying a plurality of spectral peaks included in the audio signal and in the frequency band, identifying a plurality of frequencies corresponding to the plurality of spectral peaks, and determining the average frequency based on the plurality of frequencies. In some examples, each frequency corresponding to the spectral peaks may be weighted before the average frequency is determined. The average frequency may be determined in any other way as may serve a particular implementation. For example, the average frequency may be determined by determining a center of gravity for the spectral peaks included in the audio signal.

In response to spectral analysis facility 308 identifying a feature of an audio signal, current steering management facility 304 may identify an electrode (either physical or virtual) associated with the identified feature. For example, with reference again to FIG. 4, spectral analysis facility 308 may detect a frequency of 300 Hz (which frequency may be representative of a frequency of a spectral peak, a pitch, an average frequency, etc.) within an audio signal presented to a patient. In response, current steering management facility 304 may identify an electrode to which a frequency of 300 Hz is mapped in accordance with the particular current steering range previously set by current steering management facility 304. For example, if the current steering range value is zero, current steering management facility 304 may identify virtual electrode 404-2 as the electrode to which 300 Hz is mapped. Alternatively, if the current steering range value is 0.5, current steering management facility 304 may identify virtual electrode 404-3 as the electrode to which 300 Hz is mapped. Alternatively, if the current steering range value is one, current steering management facility 304 may identify physical electrode E1 as the electrode to which 300 Hz is mapped.

Current steering management facility 304 may be further configured to direct the auditory prosthesis to apply electrical stimulation representative of the feature identified by spectral analysis facility 308 to a stimulation site associated with the electrode (physical or virtual) to which the detected frequency is mapped.

To illustrate, if the mapped electrode is a virtual electrode (e.g., one of virtual electrodes 404), current steering management facility 304 may direct the auditory prosthesis to apply electrical stimulation representative of the detected frequency by directing the auditory prosthesis to concurrently stimulate the first physical electrode (e.g., physical electrode E1) with a first current level and the second physical electrode (e.g., physical electrode E2) with a second current level. The ratio of the first current level to the second current level is based on a position of the virtual electrode within the current steering range of the stimulation channel. For example, with reference to FIG. 4, if the detected frequency is 300 Hz, and the virtual electrode to which 300 Hz is mapped is virtual electrode 404-2, an equal amount of current is applied to physical electrodes E1 and E2. However, if the virtual electrode to which 300 Hz is mapped is virtual electrode 404-3, the ratio of the first current level to the second current level is greater than one.

Alternatively, if the mapped electrode is a physical electrode (e.g., physical electrode E1 or physical electrode E2), current steering management facility 304 may direct the auditory prosthesis to apply electrical stimulation representative of the detected frequency by directing the auditory prosthesis to only stimulate the physical electrode. For example, with reference to FIG. 4, if the detected frequency is 300 Hz, and the physical electrode to which 300 Hz is mapped is physical electrode E1, all of the current is applied to physical electrode E1.

Current steering management facility 304 may be further configured to optimize a compliance voltage of an auditory prosthesis by setting a current steering range for one or more stimulation channels to a value that results in an optimum balance between performance and power conservation of the auditory prosthesis. To illustrate, with reference to FIG. 4, the compliance voltage maintained by an auditory prosthesis may be represented by $I*R*(½+\sigma/2)$, where "I" represents a total amount of current applied to physical electrodes E1 and E2, "R" represents an impedance of physical electrodes E1 and E2, and "$\sigma$" represents a current steering range associated stimulation channel 402. Accordingly, if a is equal to 1 (signifying full current steering about the midpoint of stimulation channel 402), the compliance voltage is equal to I*R. Alternatively, if $\sigma$ is equal to 0 (signifying no current steering about the midpoint of stimulation channel 402), the compliance voltage is equal to (½)*I*R. Hence, the compliance voltage is at a maximum when $\sigma$ is equal to 1 and at a minimum when $\sigma$ is equal to 0. However, the performance level of the auditory prosthesis is also at a maximum when $\sigma$ is equal to 1 and at a minimum when $\sigma$ is equal to 0. Hence, in some examples, current steering management facility 304 may balance performance and power conservation by setting the current steering range value $\sigma$ to any suitable value (e.g., 0.5) in between 0 and 1.

Returning to FIG. 3, storage facility 310 may be configured to maintain control parameter data 312 representative of one or more control parameters, which may include one or more stimulation parameters (e.g., current steering parameters) to be transmitted from sound processor 104 to auditory prosthesis 110. Storage facility 310 may be configured to maintain additional or alternative data as may serve a particular implementation.

Figure 5:
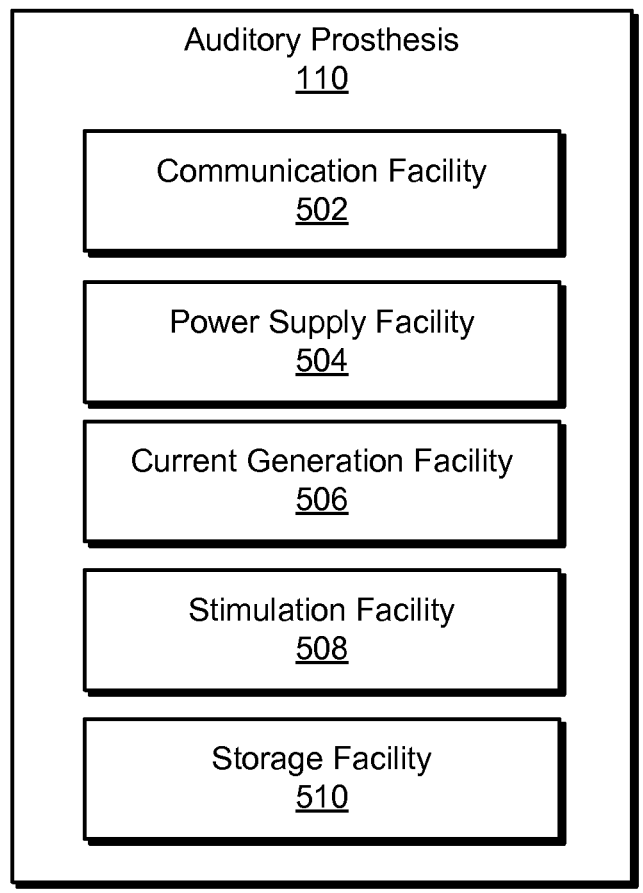
FIG. 5 illustrates exemplary components of an auditory prosthesis according to principles described herein.

FIG. 5 illustrates exemplary components of auditory prosthesis 110. As shown in FIG. 5, auditory prosthesis 110 may include a communication facility 502, a power supply facility 504, a current generation facility 506, a stimulation facility 508, and a storage facility 510, which may be in communication with one another using any suitable communication technologies. Each of these facilities 502-410 may include any combination of hardware, software, and/or firmware as may serve a particular application. For example, one or more of facilities 502-410 may include a computing device or processor configured to perform one or more of the functions described herein. Facilities 502-410 will now be described in more detail.

Communication facility 502 may be configured to facilitate communication between auditory prosthesis 110 and sound processor 104. For example, communication facility 502 may include one or more coils configured to receive control signals and/or power signals from sound processor 104. Communication facility 502 may additionally or alternatively be configured to transmit one or more status signals and/or other data to sound processor 104.

Power supply facility 504 may be configured to provide power to various components included within auditory prosthesis 110. To this end, power supply facility 504 may be configured to derive a compliance voltage from a power signal received from sound processor 104. The compliance voltage may be used by current generation facility 504 to generate stimulation current and/or by any other component within auditory prosthesis 110.

Current generation facility 506 may be configured to generate stimulation current in accordance with one or more stimulation parameters received from sound processor 104. To this end, current generation facility 506 may include one or more current generators and/or any other circuitry configured to facilitate generation of stimulation current. For example, current generation facility 506 may include an array of independent current generators each corresponding to a distinct electrode or channel. A maximum stimulation current level that each current generator is capable of producing is dependent in part on the compliance voltage produced by power supply facility 504.

Stimulation facility 508 may be configured to facilitate application of the stimulation current generated by current generation facility 506 to one or more stimulation sites within the patient in accordance with one or more stimulation parameters received from sound processor 104. In some examples, stimulation facility 508 may be configured to operate in accordance with a current steering range set by sound processor 104.

Storage facility 510 may be configured to maintain data generated and/or utilized by auditory prosthesis 110. For example, storage facility 510 may maintain data representative of one or more stimulation parameters configured to define the stimulation current generated and applied by auditory prosthesis 110.

Figure 6:
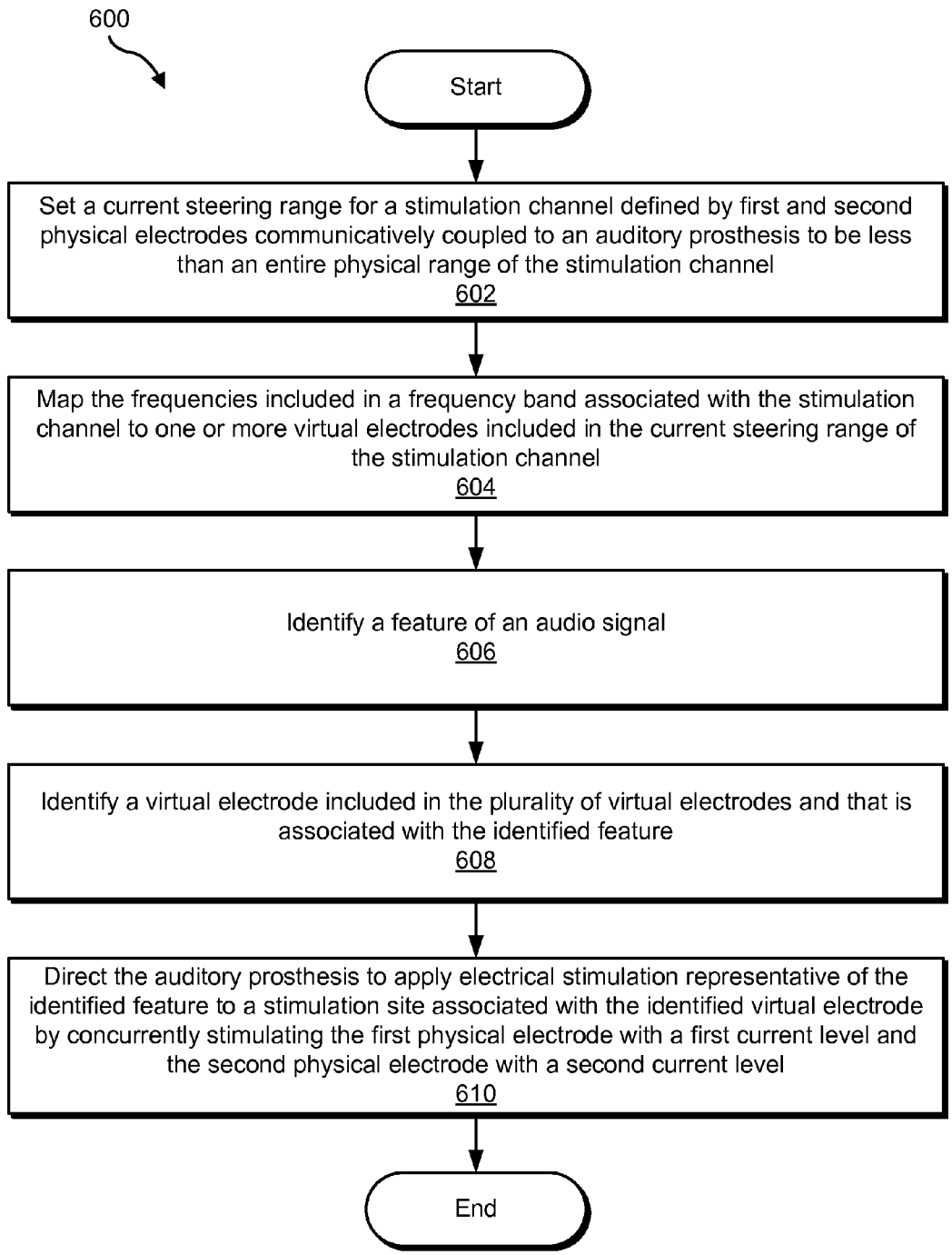
FIG. 6 illustrates an exemplary method of optimizing a compliance voltage of an auditory prosthesis according to principles described herein.

FIG. 6 illustrates an exemplary method 600 of optimizing a compliance voltage of an auditory prosthesis. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of sound processor 104.

In step 602, a sound processor sets a current steering range for a stimulation channel defined by first and second physical electrodes communicatively coupled to an auditory prosthesis to be less than an entire physical range of the stimulation channel. The current steering range is centered about the midpoint of the stimulation channel and may be set to be less than the entire physical range of the stimulation channel in any of the ways described herein. As mentioned, one benefit of limiting the current steering range in this manner is that the compliance voltage required by the auditory prosthesis is reduced relative to that needed when full current steering is employed.

In step 604, the sound processor maps the frequencies included in a frequency band associated with the stimulation channel to one or more virtual electrodes included in the current steering range of the stimulation channel. Step 604 may be performed in any of the ways described herein.

In step 606, the sound processor identifies a feature of an audio signal (e.g., an audio signal presented to the patient). Step 606 may be performed in any of the ways described herein.

In step 608, the sound processor identifies a virtual electrode associated with the identified feature. Step 608 may be performed in any of the ways described herein.

In step 610, the sound processor directs the auditory prosthesis to apply electrical stimulation representative of the identified frequency to a stimulation site associated with the identified virtual electrode by concurrently stimulating the first physical electrode with a first current level and the second physical electrode with a second current level. As described above, a ratio of the first current level to the second current level is based on a position of the identified virtual electrode within the current steering range of the stimulation channel. Step 610 may be performed in any of the ways described herein.

Figure 7:
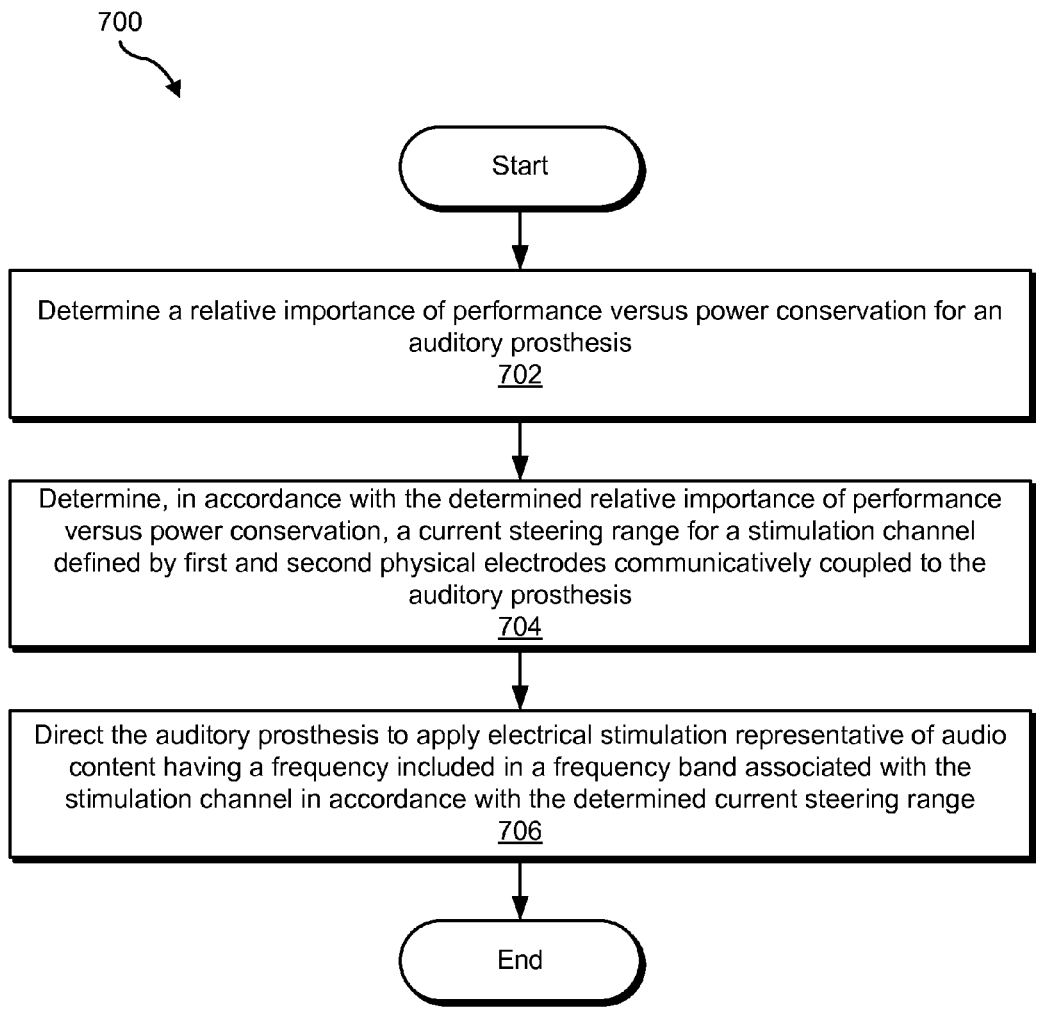
FIG. 7 illustrates another exemplary method of optimizing a compliance voltage of an auditory prosthesis according to principles described herein.

FIG. 7 illustrates another exemplary method 700 of optimizing a compliance voltage of an auditory prosthesis. While FIG. 7 illustrates exemplary steps according to one embodiment, other embodiments may omit, add to, reorder, and/or modify any of the steps shown in FIG. 7. One or more of the steps shown in FIG. 7 may be performed by any component or combination of components of sound processor 104.

In step 702, a sound processor determines a relative importance of performance versus power conservation for an auditory prosthesis. The determination may be performed in response to input provided by a user (e.g., a patient, clinician, etc.) specifying a particular relative importance. Additionally or alternatively, as will be illustrated below, the determination may be performed by the sound processor automatically.

In step 704, the sound processor determines, in accordance with the determined relative importance of performance versus power conservation, a current steering range for a stimulation channel defined by first and second physical electrodes communicatively coupled to the auditory prosthesis. The current steering range is centered about a midpoint of the stimulation channel and may be determined in any suitable manner.

In step 706, the sound processor directs the auditory prosthesis to apply electrical stimulation representative of audio content having a frequency included in a frequency band associated with the stimulation channel in accordance with the determined current steering range. Step 706 may be performed in any of the ways described herein.

Various implementations and examples of the systems and methods described herein will now be provided. It will be recognized that the implementations and examples provided herein are merely illustrative of the many different implementations and examples that may be realized in accordance with the systems and methods described herein.

In some implementations, a sound processor may set a current steering range associated with a particular stimulation channel in response to input provided to the sound processor by a user. For example, a user may manually switch between different stimulation programs by using a switch or the like included within or otherwise associated with the sound processor. Each stimulation program may specify a distinct current steering range that is to be associated with one or more stimulation channels. Hence, in response to a user switching to a different stimulation program, the sound processor may adjust one or more current steering ranges to one or more values specified by the different stimulation program.

As mentioned, a sound processor may determine a relative importance of performance versus power conservation for an auditory prosthesis and then determine, set, and/or adjust a current steering range associated with a stimulation channel in accordance with the determined relative importance. This may be performed in any suitable manner. For example, the sound processor may determine that an auditory prosthesis patient is located within a particular environment (e.g., in a noisy restaurant), listening to a particular type of audio (e.g., music), and/or in any other situation that requires a relatively high auditory prosthesis performance level. At the same time, the sound processor may determine that the need for conserving power is relatively low (e.g., by determining that an available amount of power within a battery supplying power to the auditory prosthesis is above a predetermined threshold). In response, the sound processor may increase one or more current steering ranges associated with one or more stimulation channels in order to increase a performance level of the auditory prosthesis.

Alternatively, the sound processor may determine that the auditory prosthesis patient is located within a particular environment (e.g., in a quiet room), listening to a particular type of audio (e.g., speech), and/or in any other situation that does not require a relatively high auditory prosthesis performance level. At the same time, the sound processor may determine that the need for conserving power is relatively high (e.g., by determining that an available amount of power within a battery supplying power to the auditory prosthesis is below a predetermined threshold). In response, the sound processor may decrease one or more current steering ranges associated with one or more stimulation channels in order to reduce a compliance voltage that the auditory prosthesis has to maintain and thereby reduce power consumption by the auditory prosthesis.

In some implementations, a sound processor may prevent any of the physical electrodes connected to an auditory prosthesis from being mapped to a particular frequency. In this manner, full current steering may not be used in any of the stimulation channels defined by the physical electrodes. This ensures that current will always be split among at least two physical electrodes when representing a frequency associated with an audio signal.

Figure 8:
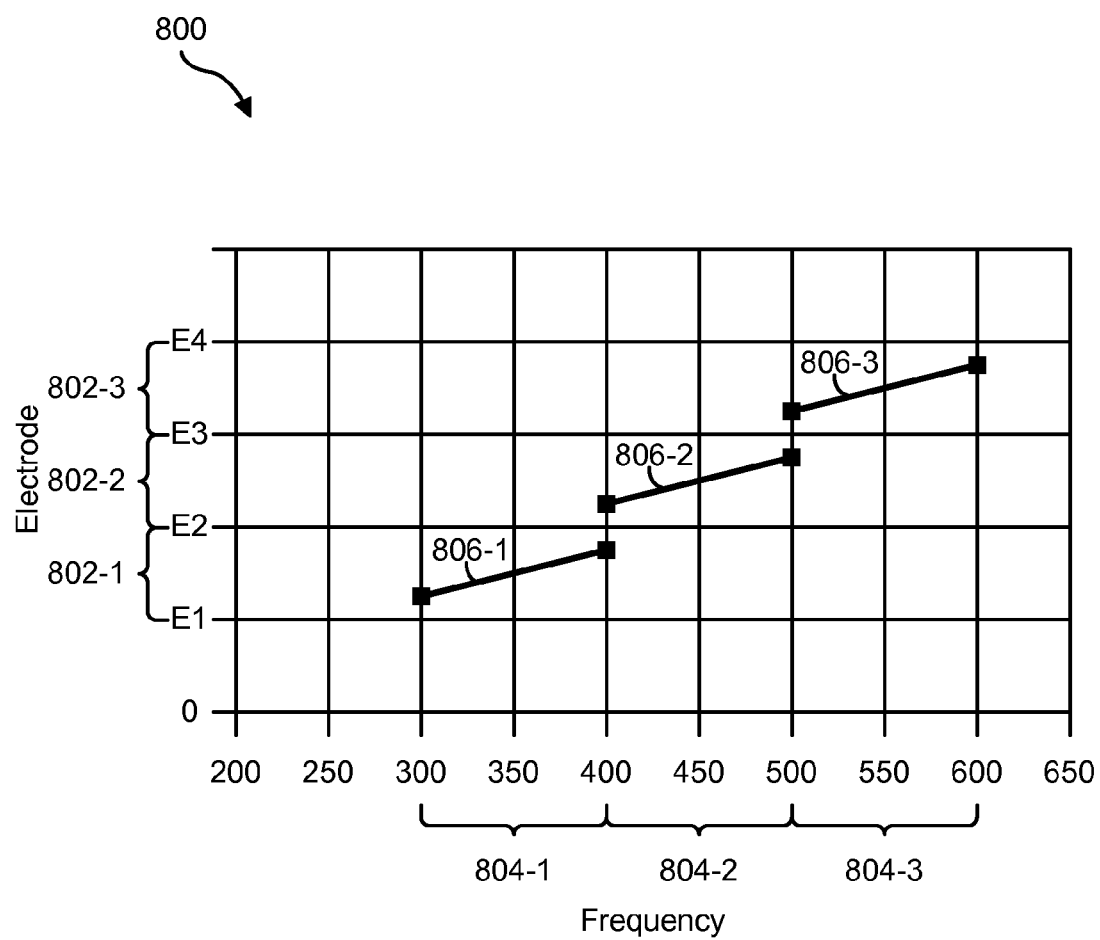
FIG. 8 shows an exemplary mapping strategy according to principles described herein.

To illustrate, FIG. 8 shows an exemplary mapping strategy 800 in which a limited current steering range is associated with each stimulation channel formed by physical electrodes E1 through E4. As shown, physical electrodes E1 and E2 define a first stimulation channel 802-1, physical electrodes E2 and E3 define a second stimulation channel 802-2, and physical electrodes E3 and E4 define a third stimulation channel 802-3. Each stimulation channel 802 has a particular frequency band 804 (e.g., frequency bands 804-1 through 804-3) associated therewith. For example, frequency band 804-1 is associated with stimulation channel 802-1, frequency band 804-2 is associated with stimulation channel 802-2, and frequency band 804-3 is associated with stimulation channel 802-3. FIG. 8 also shows a frequency-to-electrode mapping 806 (e.g., mapping 806-1 through 806-3) for each stimulation channel 802. As shown by mappings 806, none of physical electrodes E1 through E4 have a frequency mapped thereto. Rather, each frequency between 300 Hz and 600 Hz is mapped to virtual electrodes disposed in between the physical electrodes, thereby ensuring that current will always be split between two physical electrodes.

In some examples, a sound processor may be configured to detect a need to minimize interaction between adjacent stimulation channels. As used herein, "interaction between adjacent stimulation channels" (or simply "channel interaction") refers to a situation wherein electrical stimulation applied via one stimulation channel at least partially masks the electrical stimulation applied via another stimulation channel. Channel interaction may inhibit the ability of a patient to perceive fine structure information (e.g., information that facilitates the perception of pitch, spatial location, etc. of an audio signal) applied via either one of the stimulation channels. The detection of a need to minimize channel interaction may be performed in response to user input (e.g., user input indicating a request to decrease channel interaction) and/or automatically as may serve a particular implementation. In response, the sound processor may decrease the current steering ranges associated with each stimulation channel, thereby increasing a buffer between each current steering range and decreasing interaction between the two stimulation channels.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   a current steering management facility that sets a current steering range for a stimulation channel defined by first and second physical electrodes communicatively coupled to an auditory prosthesis to be less than an entire physical range of the stimulation channel, the current steering range being centered about a midpoint of the stimulation channel;
   a mapping facility communicatively coupled to the current steering management facility and that maps each frequency included in a frequency band associated with the stimulation channel to a virtual electrode included in a plurality of virtual electrodes included in the current steering range of the stimulation channel; and
   a spectral analysis facility communicatively coupled to the mapping facility and that identifies a feature of an audio signal;
   wherein the current steering management facility further identifies a virtual electrode included in the plurality of virtual electrodes and that is associated with the identified feature, and
   directs the auditory prosthesis to apply electrical stimulation representative of the identified feature to a stimulation site associated with the identified virtual electrode by concurrently stimulating the first physical electrode with a first current level and the second physical electrode with a second current level; and
   wherein a ratio of the first current level to the second current level is based on a position of the identified virtual electrode within the current steering range of the stimulation channel.

2. The system of claim 1, wherein the feature is a dominant frequency included in the audio signal, and wherein the spectral analysis facility identifies the dominant frequency by:
   identifying a spectral peak included in the audio signal and within the frequency band; and
   designating a frequency of the spectral peak as the dominant frequency.

3. The system of claim 1, wherein the feature is a pitch of the audio signal.

4. The system of claim 3, wherein the spectral analysis facility identifies the pitch of the audio signal by:
   identifying a plurality of spectral peaks included in the audio signal;
   identifying a plurality of frequencies corresponding to the plurality of spectral peaks; and
   identifying the pitch based on the plurality of frequencies.

5. The system of claim 4, wherein the current steering management facility identifies the virtual electrode associated with the pitch by identifying one or more virtual electrodes included in the plurality of virtual electrodes and that correspond to one or more of the plurality of frequencies corresponding to the plurality of spectral peaks.

6. The system of claim 1, wherein the current steering management facility directs the auditory prosthesis to apply the electrical stimulation during a stimulation frame, and wherein the feature is a pitch of the audio signal during a prior stimulation frame that temporally precedes the stimulation frame.

7. The system of claim 1, wherein the feature is an average frequency of the audio signal within the frequency band.

8. The system of claim 7, wherein the spectral analysis facility identifies the average frequency by:
   identifying a plurality of spectral peaks included in the audio signal and in the frequency band;
   identifying a plurality of frequencies corresponding to the plurality of spectral peaks; and
   determining the average frequency based on the plurality of frequencies.

9. The system of claim 8, wherein the determining of the average frequency comprises weighting each frequency included in the plurality of frequencies corresponding to the plurality of spectral peaks in accordance with a magnitude of each of the plurality of spectral peaks.

10. The system of claim 1, wherein the current steering management facility sets the current steering range in response to input provided to the sound processor by a user.

11. The system of claim 1, wherein the current steering management facility:
   determines a relative importance of performance versus power conservation for the auditory prosthesis; and
   automatically sets the current steering range in accordance with the determined relative importance.

12. A method comprising:
   setting, by a sound processor, a current steering range for a stimulation channel defined by first and second physical electrodes communicatively coupled to an auditory prosthesis to be less than an entire physical range of the stimulation channel, the current steering range being centered about a midpoint of the stimulation channel;
   mapping, by the sound processor, each frequency included in a frequency band associated with the stimulation channel to a virtual electrode included in a plurality of virtual electrodes included in the current steering range of the stimulation channel;
   identifying, by the sound processor, a feature of an audio signal;
   identifying, by the sound processor, a virtual electrode included in the plurality of virtual electrodes and that is associated with the identified feature; and
   directing, by the sound processor, the auditory prosthesis to apply electrical stimulation representative of the identified feature to a stimulation site associated with the identified virtual electrode by concurrently stimulating the first physical electrode with a first current level and the second physical electrode with a second current level;
   wherein a ratio of the first current level to the second current level is based on a position of the identified virtual electrode within the current steering range of the stimulation channel.

13. The method of claim 12, wherein the feature is a dominant frequency included in the audio signal, and wherein the identifying of the dominant frequency comprises:

identifying a spectral peak included in the audio signal and within the frequency band; and designating a frequency of the spectral peak as the dominant frequency.

14. The method of claim 12, wherein the feature is a pitch of the audio signal.

15. The method of claim 14, wherein the identifying of the feature of the audio signal comprises:

identifying a plurality of spectral peaks included in the audio signal;

identifying a plurality of frequencies corresponding to the plurality of spectral peaks; and identifying the pitch based on the plurality of frequencies.

16. The method of claim 15, wherein the identifying of the virtual electrode associated with the pitch comprises identifying one or more virtual electrodes included in the plurality of virtual electrodes and that correspond to one or more of the plurality of frequencies corresponding to the plurality of spectral peaks.

17. The method of claim 12, auditory prosthesis applies the electrical stimulation during a stimulation frame, and wherein the feature is a pitch of the audio signal during a prior stimulation frame that temporally precedes the stimulation frame.

18. The method of claim 12, wherein the feature is an average frequency of the audio signal within the frequency band.

19. The method of claim 18, further comprising identifying the average frequency by:

identifying a plurality of spectral peaks included in the audio signal and in the frequency band;

identifying a plurality of frequencies corresponding to the plurality of spectral peaks; and determining the average frequency based on the plurality of frequencies.

20. The method of claim 19, wherein the determining of the average frequency comprises weighting each frequency included in the plurality of frequencies corresponding to the plurality of spectral peaks in accordance with a magnitude of each of the plurality of spectral peaks.

\* \* \* \* \*